(12) United States Patent
Törnsten et al.

(10) Patent No.: US 10,532,159 B2
(45) Date of Patent: Jan. 14, 2020

(54) INJECTION DEVICE

(71) Applicant: NESTLE SKIN HEALTH S.A., Lausanne (CH)

(72) Inventors: Jonas Törnsten, Uppsala (SE); Max Blomqvist, Uppsala (SE); Conny Pettersson, Vallingby (SE)

(73) Assignee: NESTLÉ SKIN HEALTH S.A., Lausanne (CH)

( * ) Notice: Subject to any disclaimer, the term of this patent is extended or adjusted under 35 U.S.C. 154(b) by 0 days.

(21) Appl. No.: 15/104,436

(22) PCT Filed: Nov. 10, 2014

(86) PCT No.: PCT/EP2014/074183
§ 371 (c)(1),
(2) Date: Jun. 14, 2016

(87) PCT Pub. No.: WO2015/090731
PCT Pub. Date: Jun. 25, 2015

(65) Prior Publication Data
US 2016/0310674 A1      Oct. 27, 2016

(30) Foreign Application Priority Data

Dec. 20, 2013   (EP) .................................... 13199097

(51) Int. Cl.
*A61M 5/315*   (2006.01)
*A61M 5/24*    (2006.01)
*A61M 5/20*    (2006.01)

(52) U.S. Cl.
CPC .......... *A61M 5/31515* (2013.01); *A61M 5/20* (2013.01); *A61M 5/24* (2013.01);
(Continued)

(58) Field of Classification Search
CPC .......... A61M 2005/31516; A61M 5/20; A61M 5/24; A61M 5/31505; A61M 5/31515
See application file for complete search history.

(56) References Cited

U.S. PATENT DOCUMENTS 4,299,238 A * 11/1981 Baidwan ............ A61B 5/15003
                                                        600/576
4,677,980 A *  7/1987 Reilly .................. A61M 5/007
                                                        128/DIG. 1
(Continued)

FOREIGN PATENT DOCUMENTS

EP         2 332 602 A1    6/2011
WO    WO 00/32259 A2       6/2000
(Continued)

OTHER PUBLICATIONS

International Search Report (PCT/ISA/210) dated Apr. 9, 2015, by the European Patent Office as the International Searching Authority for International Application No. PCT/EP2014/074183.

*Primary Examiner* — Quynh-Nhu H. Vu
(74) *Attorney, Agent, or Firm* — Sunit Talapatra; Foley & Lardner LLP

(57) ABSTRACT

An injection device for delivering a liquid composition, including a generally elongated housing, arranged to hold an exchangeable cartridge containing the liquid composition. The housing includes a drive device, and a plunger rod connected with the drive device and connected to a plunger within the cartridge, when the cartridge is held at the housing, for driving the plunger within the cartridge. The plunger includes a rod connector connected with a front end portion of the plunger rod. The rod connector comprises a rod stop portion, wherein there is a longitudinal play between the plunger rod on one hand and the entrance opening and the rod stop portion on the other hand, thereby enabling the front end portion to move back and forth (Continued)

between the entrance opening and the rod stop portion without moving the plunger.

14 Claims, 5 Drawing Sheets

(52) U.S. Cl.
CPC .............. *A61M 5/31505* (2013.01); *A61M 2005/31516* (2013.01)

(56) References Cited

U.S. PATENT DOCUMENTS

| | | | | |
|---|---|---|---|---|
| 5,201,709 | A * | 4/1993 | Capra | A61M 5/5066 604/110 |
| 5,411,488 | A * | 5/1995 | Pagay | A61M 5/31513 604/218 |
| 5,947,935 | A * | 9/1999 | Rhinehart | A61M 5/14546 604/131 |
| 6,312,412 | B1 | 11/2001 | Saied et al. | |
| 2003/0153877 | A1 * | 8/2003 | Huang | A61M 5/322 604/240 |
| 2004/0158205 | A1 | 8/2004 | Savage | |
| 2005/0015056 | A1 | 1/2005 | Duchon et al. | |
| 2008/0281278 | A1 * | 11/2008 | Williams, Jr. | A61M 5/14526 604/264 |
| 2009/0299328 | A1 | 12/2009 | Mudd et al. | |
| 2010/0256486 | A1 * | 10/2010 | Savage | A61M 5/007 600/432 |
| 2012/0226157 | A1 * | 9/2012 | Hack | A61M 5/14546 600/432 |
| 2014/0330206 | A1 | 11/2014 | Moore | |

FOREIGN PATENT DOCUMENTS

| | | |
|---|---|---|
| WO | WO 02/04049 A1 | 1/2002 |
| WO | WO 2013/079643 A1 | 6/2013 |

* cited by examiner

INJECTION DEVICE

FIELD OF THE INVENTION

The present invention relates to an injection device for delivering liquid compositions, such as viscous gels of e.g. hyaluronic acid.

BACKGROUND OF THE INVENTION

WO 2000/32259 discloses an injection device for injecting a medicament. It is noted that the prior art injection device comprises two injectors for injecting first a numbing agent with a first needle, and then the medicated liquid with a second needle, which inserted deeper into the tissue. The injectors have a similar construction though. In order to simplify the description of the prior art injection device, it will be describe from a one injector perspective. Thus, for each injector, the injection device primarily comprises two main parts, a cartridge containing a liquid and having a needle, and an operation part having a cartridge holder, a plunger rod, connectable to a plunger of the cartridge, and a drive device for driving the plunger rod within the liquid container of the cartridge, such that the liquid is expelled from the container through an opening of a needle provided at a front end of the container. The cartridge is disposable, i.e. it is exchangeable for a new cartridge after use. More particularly, the plunger comprises a releasable snap lock for the plunger rod, as follows. The plunger comprises a cup-shaped receptacle for receiving a ball-shaped end of the plunger rod. The mouth of the receptacle is partly covered by radially inwardly extending finger projections, which define a circular opening having a smaller diameter than the ball-shaped end. Since the finger projections are a bit flexible, the ball-shaped end can be forced passed them into the receptacle, and be withdrawn out of the receptacle, while still being retained in the receptacle during operation of the plunger. Thereby, in short the injection device is operated as follows. The cartridge is mounted at the cartridge holder of the operation part, the injection device is activated to move the plunger rod forward into abutment against the finger projections of the receptacle. By moving the plunger rod further forwards, the container is moved forwards, and thus the needle is inserted. When the needle is fully inserted, the plunger rod, by further forward motion thereof, enters the receptacle passed the finger projections. Then the liquid is expelled by driving the plunger rod to move further forwards. When the plunger rod is moved rearwards again, the plunger is retracted to a rear stop, then the needle is retracted, and, finally, the plunger rod leaves the receptacle, and the cartridge can be removed.

The above-described known injection device may work well for one time injections. However, another large application area for injection devices is multiple injections with the same cartridge, such as for different skin treatments, where a sub-amount of the liquid contained in the cartridge is injected at each injection. However, then a problem is encountered when pulling out the needle for the next injection. Due to the viscosity of the liquid, the needle is likely to drool when it is pulled out.

SUMMARY OF THE INVENTION

It would be advantageous to reduce the drooling of the injection device when used for multiple consecutive injections.

To better address this concern, in a first aspect of the invention there is presented an injection device for delivering a liquid composition, comprising a generally elongated housing, arranged to hold an exchangeable cartridge containing the liquid composition, said housing comprising a drive device, and a plunger rod connected to a plunger within the cartridge, when the cartridge is held at the housing, for driving the plunger within the cartridge. The plunger comprises a rod connector connected with a front end portion of the plunger rod. The rod connector has an entrance opening defined by wall sections of the rod connector, the width of the entrance opening being smaller than the width of the front end portion, and the width of a rod portion adjacent to and rear of the front end portion at the most corresponding to the width of the entrance opening. The wall sections are resilient for enabling the front end portion to pass the entrance opening upon exerting a force on the wall sections. The rod connector comprises a rod stop portion. There is a longitudinal play between the plunger rod on one hand and the entrance opening and the rod stop portion on the other hand, thereby enabling the front end portion to move back and forth between the entrance opening and the rod stop portion without moving the plunger. The play makes it possible to reverse the plunger rod slightly to release the pressure applied to the viscous liquid, whereby the output of the liquid stops, while keeping the needle filled with the liquid. Without the play, if reversing the plunger rod, the plunger would be pulled back the same distance, which could often be an undesirably long distance, in excess of the very pressure release.

In accordance with an embodiment of the injection device, the drive unit is arranged to automatically move the plunger rod rearwards after being operated, by the user, for moving the plunger rod forwards to insert liquid, wherein the length of the rearward movement at most amounts to the length of the longitudinal play. By programming the injection device to make this automatic movement, excessive reversal caused by a user operating the injection device is prevented.

In accordance with an embodiment of the injection device, the rod connector comprises a base portion connected with the wall sections at a front end of the wall sections.

In accordance with an embodiment of the injection device, the rod stop portion is connected with the base portion.

In accordance with an embodiment of the injection device, at least one of the wall sections comprising an inner surface, and a heel portion extending radially inwards from the inner surface at a rear end of the wall section, at said entrance opening.

In accordance with an embodiment of the injection device, said at least one wall section comprising a resilient portion protruding from an outer surface of said at least one wall section and being arranged to abut against an inner surface of a liquid container comprised in the cartridge.

In accordance with an embodiment of the injection device, said at least one wall section having a front wall portion, connected with the base portion, and a rear wall portion hingedly connected with the front wall portion.

In accordance with an embodiment of the injection device, the front end portion of the plunger rod comprises a frustoconical portion having its top at the front end of the plunger rod.

In accordance with an embodiment of the injection device, the front end portion of the plunger rod comprises a circumferential engagement surface at a rear end of the front end portion, the engagement surface being arranged to engage with the plunger, at the entrance opening, for moving the plunger rearwards.

In accordance with an embodiment of the injection device, the wall sections comprise at least one complementary engagement surface for engagement with the engagement surface of the plunger rod, at the entrance opening, said at least one complementary engagement surface comprising an inclined surface leaning inwards in a rearward direction.

In accordance with an embodiment of the injection device, the plunger rod is rotatably attached for rotation about a longitudinal axis thereof, and is arranged to be rotated in order to be longitudinally moved.

In accordance with an embodiment of the injection device, the rod stop portion comprises a centre pin protruding rearwards from a front end of the rod connector at a centre thereof.

BRIEF DESCRIPTION OF THE DRAWINGS

The invention will now be described in more detail and with reference to the appended drawings in which.

DESCRIPTION OF EMBODIMENTS

Figure 1:
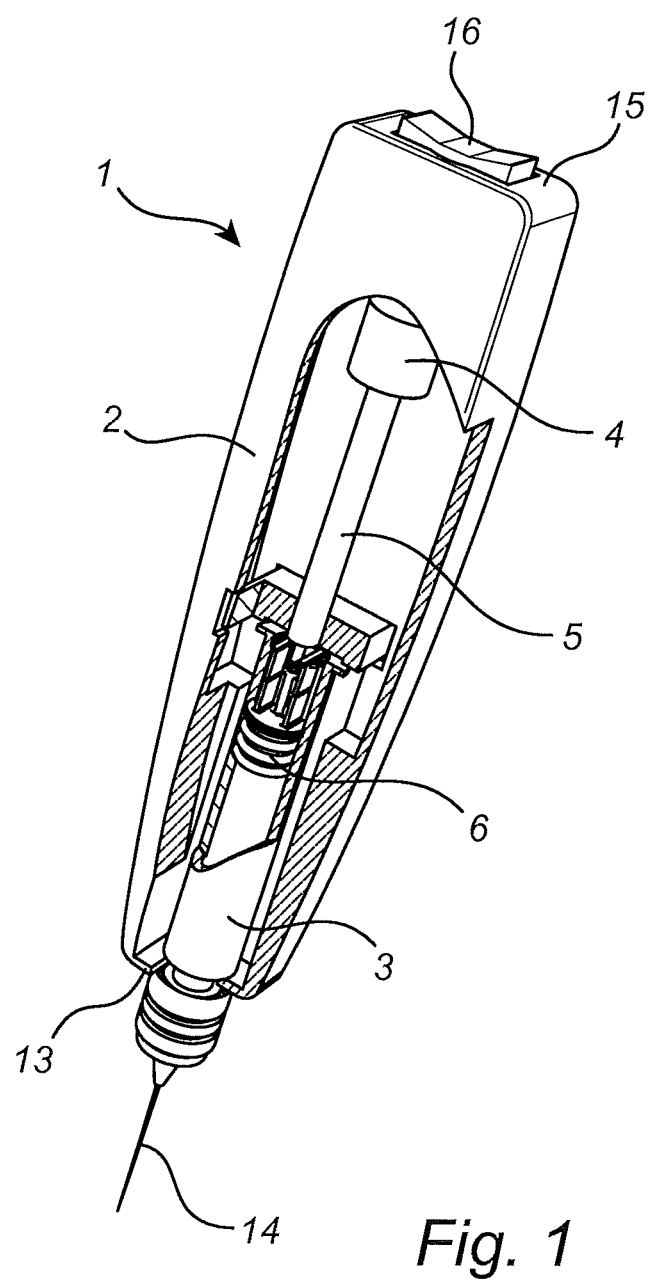
FIG. 1 is a perspective and partly cutaway view showing an embodiment of an injection device according to the present invention.
Figure 8:
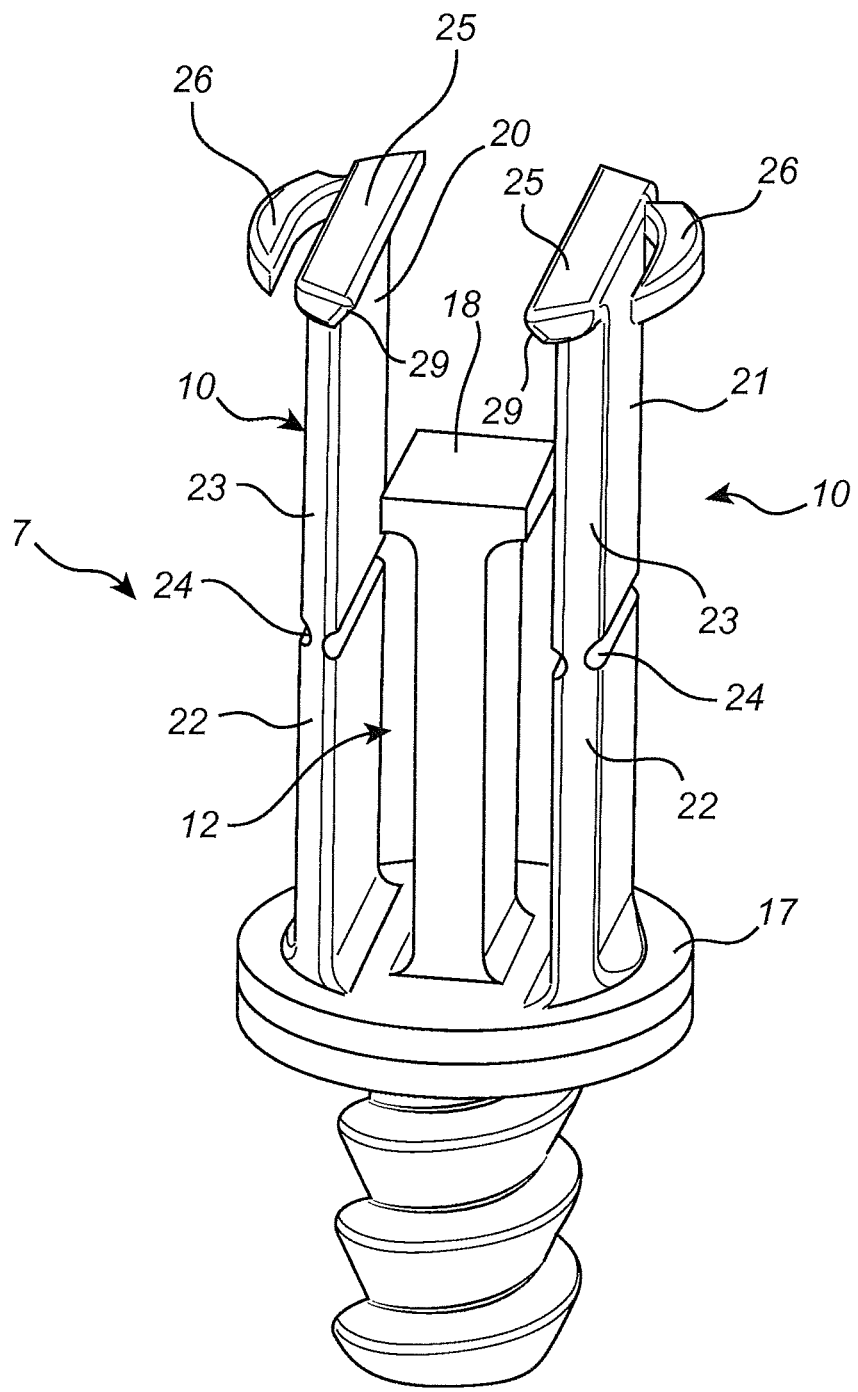
FIG. 8 is a perspective view of a rod connector comprised in the injection device of FIG. 1.

An overall view of an embodiment of the injection device is shown in FIG. 1. The injection device 1 comprises a generally elongated housing 2, arranged to hold an exchangeable cartridge 3 comprising a container 27 containing a liquid composition to be injected, and a sleeve 27a enclosing the container 27 and being configured for an accurate and engaging mounting of the cartridge 3 at the housing 2. It should be noted, though, that embodiments without the sleeve 27a are possible as well. In FIG. 1 the injection device 1 is shown with a cartridge 3 held at the housing 2, here more particularly mounted therein. The injection device 1 has a front end 13, where the injection needle 14 of the cartridge 3 is located, and a rear end 15 opposite of the front end 13. The housing 2 comprises a drive device 4, and a plunger rod 5, which is connected with the drive device 4, and which is connectable to a plunger 6 within the cartridge 3 for driving the plunger within the cartridge. An operation button 16 for respective forward and rearward operation of the plunger rod 5, is arranged at the rear end 15. This is just an illustrative example. The button can be arranged at other positions of the housing 2, and there can be more than one button, etc. More particularly, in this embodiment, the plunger rod 5 is rotatably attached to the drive device 4 for rotation about a longitudinal axis of the plunger rod 5, and is arranged to be rotated in order to be longitudinally moved. Referring to the other figures, the plunger 6 comprises a rod connector 7 for connecting with a front end portion 8 of the plunger rod 5, and a front plunger portion 7a, which is connected with the rod connector 7, and which is configured to seal the container 27 and to contact the liquid therein. For instance, the rod connector 7 and the front plunger portion 7a are separately manufactured and fitted together with a screw joint at an appropriate occasion. The rod connector 7 has an entrance opening 9 defined by wall sections 10 of the rod connector 7. The width of the entrance opening 9 is smaller than the width of the front end portion 8, and the width of a rod portion 11 adjacent to and rear of the front end portion 8 is at most the same as, and preferably smaller than, the width of the entrance opening 9. The wall sections 10 are resilient for enabling the front end portion 8 to pass the entrance opening 9 upon exerting a large enough force on the wall sections 10. The rod connector 7 comprises a rod stop portion 12, wherein there is a longitudinal play between the front end portion 8 of the plunger rod 5 on one hand and the entrance opening 9 and the rod stop portion 12 on the other hand. In other words, the distance between the entrance opening 9 and the rod stop portion 12 exceeds the length of the front end portion 8. Thereby it is possible for the front end portion 8 to move back and forth between the entrance opening 9 and the rod stop portion 12 without moving the plunger 6. More particularly, as shown in FIG. 8, the rod connector 7 comprises a base portion 17, here a circular base plate, at a front end of the rod connector 7, and two wall sections 10, which are attached to the base portion 17 and extend rearwards thereof opposite to each other. Furthermore, the rod stop portion 12 is connected with the base portion 17 between the wall sections 10. The rod stop portion 12 comprises a centre pin protruding rearwards from the base portion 17 at a centre thereof and ending at a free end, where the rod stop portion 12 is anvi shaped, and is ended with a flat abutment surface 18.

The front end portion 8 of the rod 5 is frustoconically shaped having its top at the front end of the plunger rod 5, and thus it is ended with a flat end surface 19, which is arranged to abut against the abutment surface 18 in an injection position, as will be further explained below. The frustoconical shape facilitates passage of the entrance opening 9.

Each wall section 10 is generally plate shaped and has an inner surface 20, an outer surface 21, a front wall portion 22, connected with the base portion 17, and a rear wall portion 23 connected with the front wall portion 22 via a flexible joint 24. The rear wall portion 23 comprises a heel portion 25 extending radially inwards from the inner surface 20 at a rear end of the rear wall portion 23, at said entrance opening 9, and a resilient portion 26 protruding from the outer surface 21. When the rod connector 7 has been assembled with the front plunger portion 7a and the assembled plunger 6 has been inserted into the container 27 comprised in the cartridge 3, the resilient portions 26 abut against an inner surface of the liquid container 27. As an alternative assembling process, the front plunger portion 7a alone is mounted in the container 27, in conjunction with filling the container 27, and the rod connector 7 is mounted at a later stage. Each resilient portion 26 is constituted by an arc shaped tongue attached at its one end at the outer surface 21, and extends circumferentially and alongside of the heel portion 25 at a small distance from the outer surface 21.

The front end portion 8 of the plunger rod 5 comprises a circumferential engagement surface 28 at a rear end of the front end portion 8, the engagement surface 28 being arranged to engage with the plunger 6, at the entrance opening 9, for moving the plunger 6 rearwards. Each heel portion 25 comprises a complementary engagement surface 29 for engagement with the engagement surface 28 of the plunger rod 8, at the entrance opening 9. The complementary engagement surface 29 has an inclined surface leaning inwards, i.e. towards the longitudinal centre of the rod connector 7, in a rearward direction.

Figure 2:
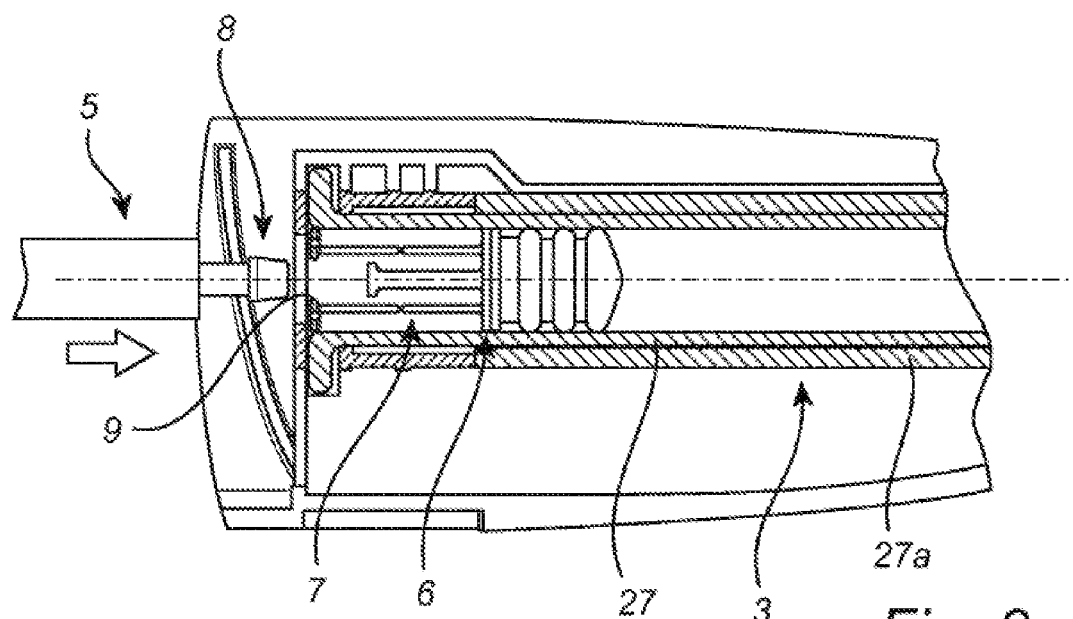
FIGS. 2 to 7 are partly sectional views showing a part of the injection device of FIG. 1 in different operational stages.
Figure 3:
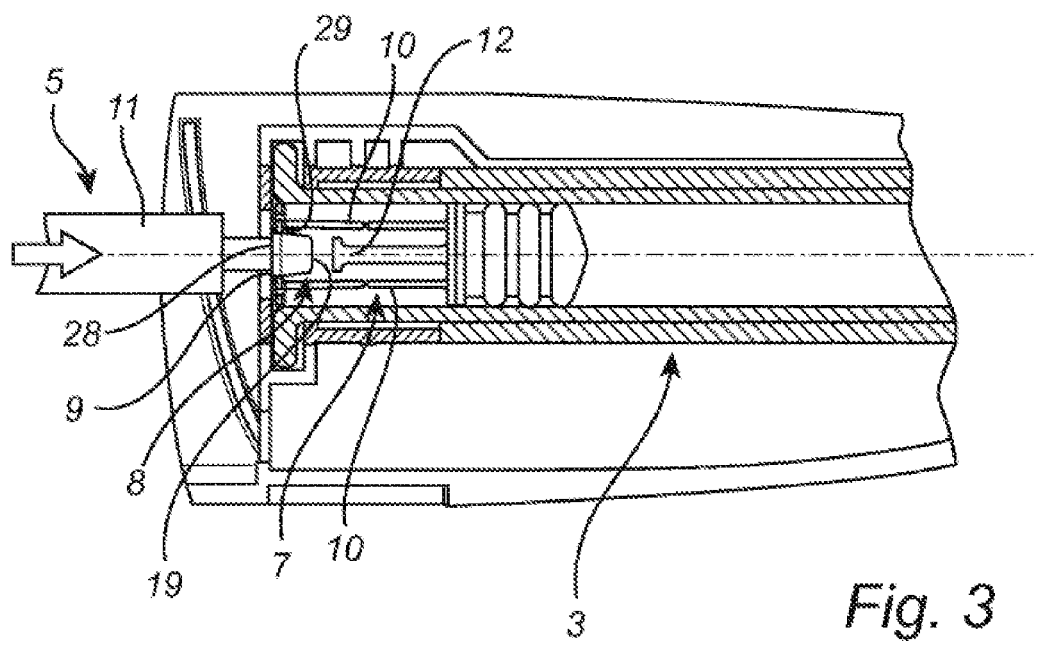
Figure 4:
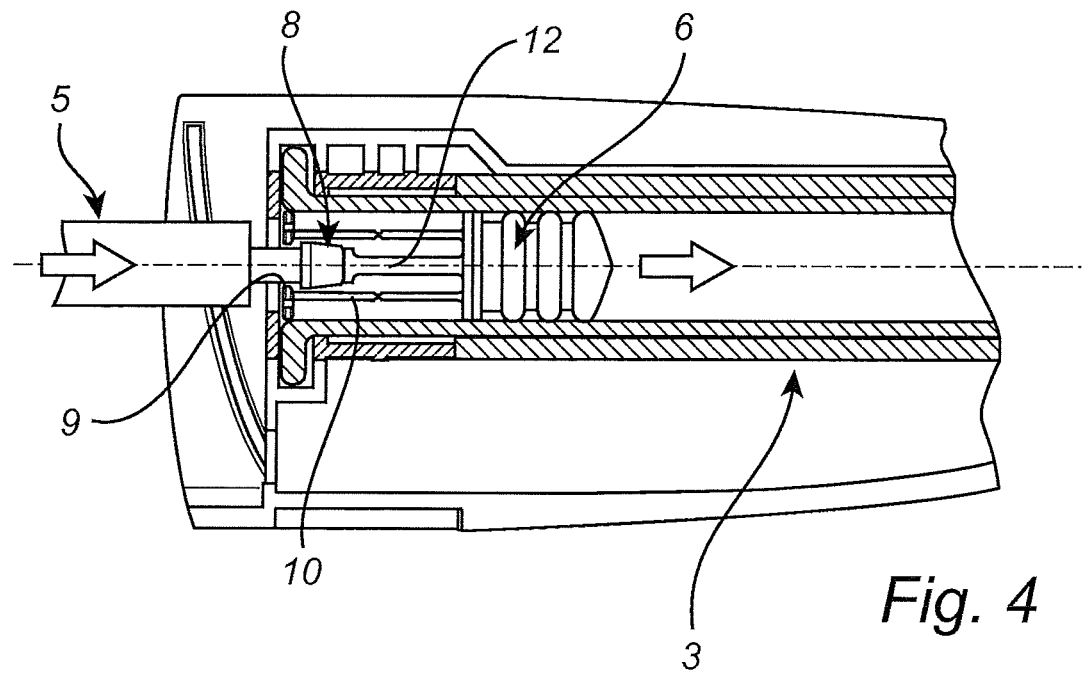

Referring to FIGS. 2-7, the injection device 1 is operated as follows. After having inserted a cartridge 3 into the housing 2, the plunger 6 is in its rearmost position, and the plunger rod 5 is positioned at the rear of the plunger 6, as shown in FIG. 2. Then the drive device 4 is activated by means of the operation button 16 for forwards operation, the plunger rod 5 is driven forward, and the front end portion 8 of the plunger rod 5 is entered into the rod connector 7 passed the entrance opening 9, by pushing the wall sections 10 aside, as shown in FIG. 3. More particularly, each wall section 10 is bent at the flexible joint 24, such that the rear wall portion 23 is inclined outwards. During this entrance, the resilient portions 26 are compressed, i.e. forced closer to the outside surfaces 21, and thereby tensioned. When the front end portion 8 has fully passed the heel portions 25 at the entrance opening 9, the resilient portions 26 return to their idle position and the entrance opening 9 is closed to its original width. The front end portion 8 is now located within the space between the heels 25 and the abutment surface 18 of the rod stop portion 12. It takes a certain fore to enter the front end portion into the rod connector 7. For a situation where the needle 14 after the interconnection of the rod 5 and plunger 6, and more particularly the front end portion 8 and the rod connector 7, the plunger 6 is not movable, due to the incompressible liquid of the container 27. However, if the needle is mounted before driving the plunger rod into connection with the plunger 6, then the entrance force needed will have to smaller than the resistance caused by the viscosity of the liquid and the friction against the wall of the container 27. Alternatively, some kind of additional mechanical hindrance can be provided, such as the circumferential rib (356) shown in WO0032259. At further forward movement of the plunger rod 5, its end surface 19 abuts against the abutment surface 18 of the rod stop portion 12, and the plunger rod 5 starts pushing the plunger 6 forward, thereby ejecting the liquid through the needle 14, as shown in FIG. 4.

Figure 5:
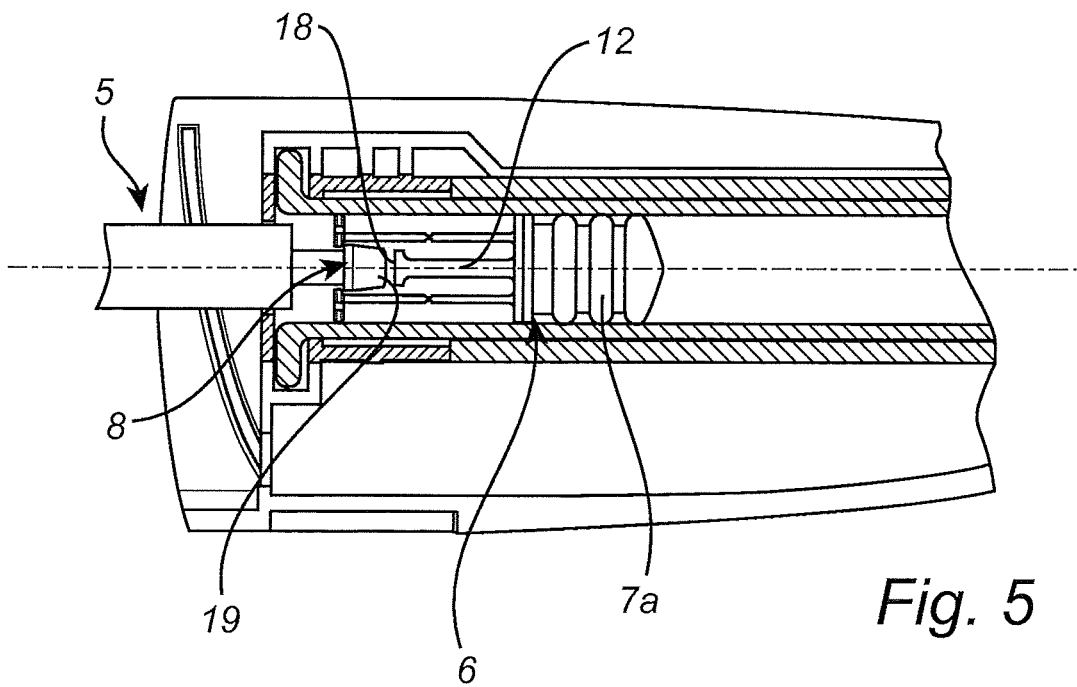

When the user stops operating the operation button 16, the forward rotational movement of the plunger rod 5 is stopped, and additionally, the injection device 1 is arranged, i.e. its drive unit 4 is programmed, to reverse the plunger rod a small distance, as shown in FIG. 5. This distance is to be just enough to cause a small gap between the end surface 19 of the front end portion 8 and the abutment surface 18 of the rod stop portion 12. Thereby the pressure exerted on the liquid by the plunger 6, and more particularly by the front plunger portion 7a, is relieved, and the ejecting of the liquid is fully stopped. If the plunger rod 5 would not be reversed, the pressure would decrease slowly for a short time period during a continued ejection of liquid. Consequently, due to the play between the front end portion 8 and the rod stop portion 12 and the heels 25, respectively, drooling is prevented without actively moving the plunger 6 rearwards. Consequently, the reversal of the plunger rod 5 should be short enough not to cause a pull back of the plunger 6, which would otherwise cause an undesired aspiration, or intake of air or body liquids in the needle.

Figure 6:
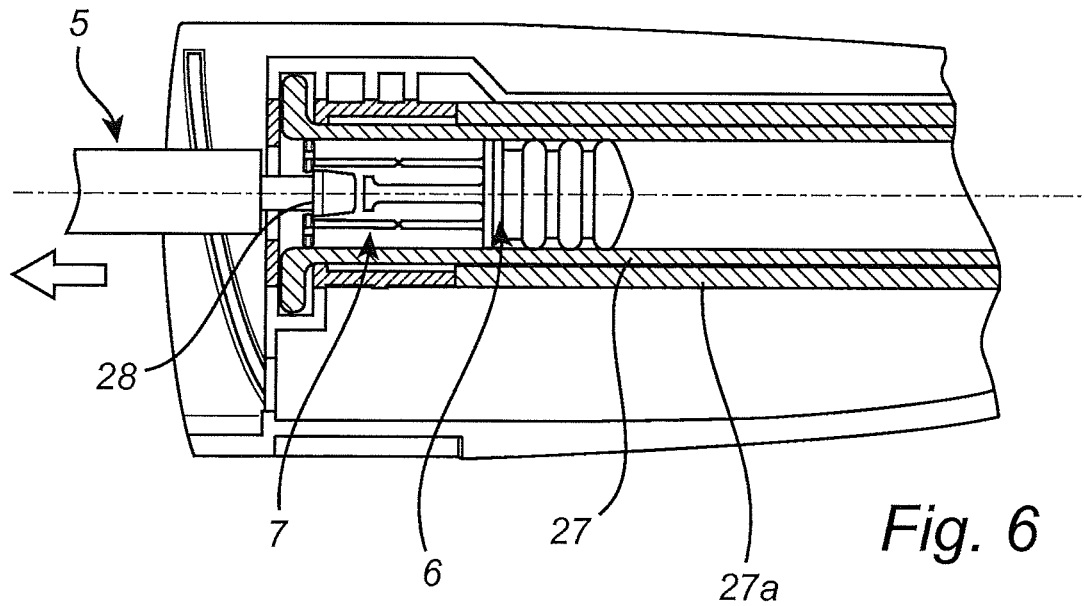
Figure 7:
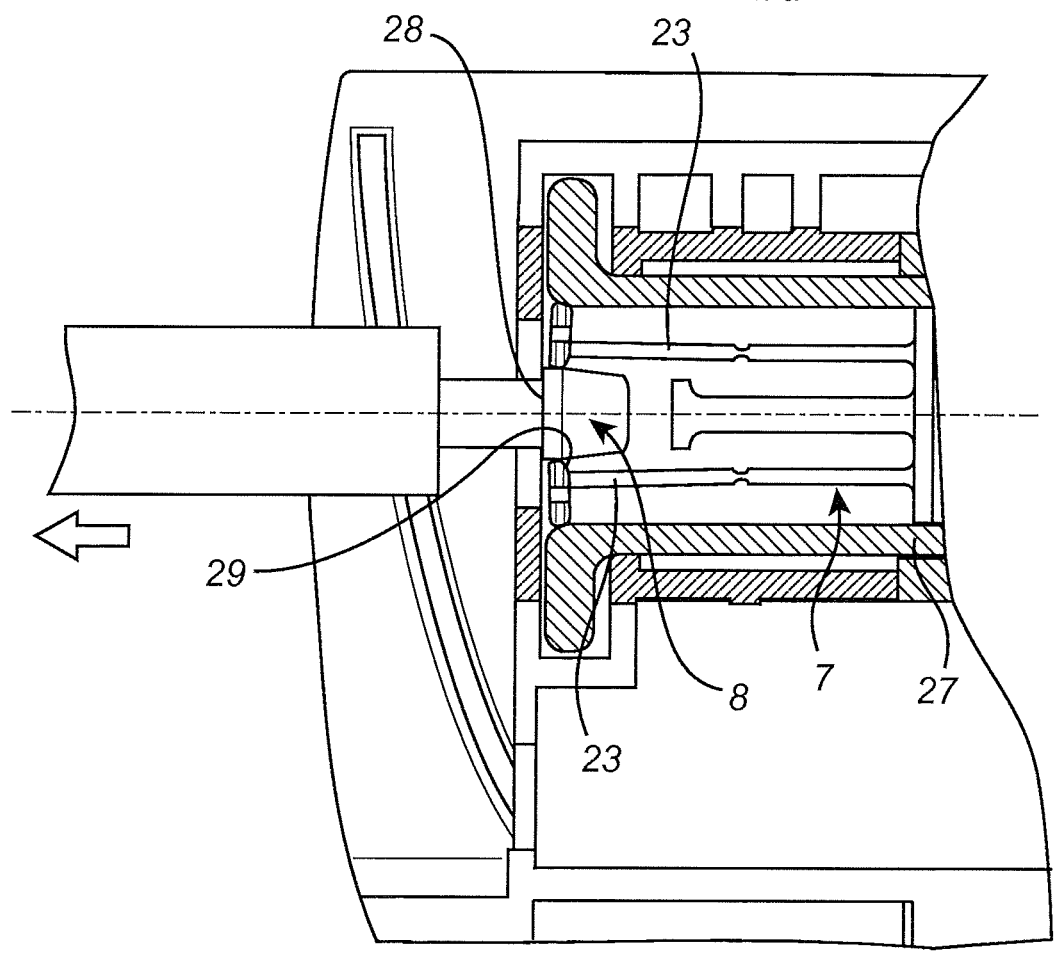

By continued intermittent operation of the operation button 16 for forward movement, several more minor injections can be performed in the same way until the container 27 is emptied, or the injection operation is finished for some other reason. In order to then reverse the plunger 6, the operation button 16 is operated for rearward operation, causing the plunger rod 5 to be retracted, as shown in FIG. 6. When the circumferential engagement surface 28 engages with the complementary engagement surfaces 29, the plunger 6 is pulled rearwards until it reaches the rear end of the container 27, and the cartridge 3. The rod connector 7 is stopped, but the plunger rod 5 continues rearwardly, while the engagement surface 28 slides across the inclined surfaces of the complementary engagement surfaces 29. This causes the rear wall portions 23 to bend outwards and let the front end portion 8 pass the entrance opening 9 and leave the rod connector 7. Then it is possible to remove the used cartridge 3.

Another operation that is often performed in conjunction with injections is aspiration, i.e. that the plunger 6 of the device 1 is reversed far enough to cause a suction into the needle 14 and container 27. During the reversal, the front end portion 8 of the plunger rod 5 engages with the complementary engagement surfaces 29, and pulls the plunger 6 along with it. This is possible due to the well tuned resilient wall portions 10, and in particular their resilient portions 26, which are strong enough to keep the entrance opening 9 in its idle position during the reversal, while being week enough to enable withdrawal of the front end portion 8 when the plunger 6 reaches its rearmost position, and enabling entrance of the front end portion 8 without moving the plunger 6 forwards, as has been described above. The shape of the front end portion 8 and its surfaces, in conjunction with the complementary engagement surfaces also contribute to enhance the entrance of the front end portion 8 into the rod connector 7, and to prevent non-intentional withdrawal of the front end portion 8 from the rod connector 7 at reversal of the plunger rod 5. It should be noted that the flexible joints add an amount of bending stress, forming a total counter force in conjunction with the resilient portions 26. However, at least in the illustrated embodiment the bending stress is negligible relative to the spring force of the resilient portions 26.

While the invention has been illustrated and described in detail in the drawings and foregoing description, such illustration and description are to be considered illustrative or exemplary and not restrictive; the invention is not limited to the disclosed embodiments.

For instance, the plunger rod can be driven in alternative ways, such as to give it a reciprocating movement, by means of an appropriate transmission of the rotational movement generated by the drive device to a longitudinal movement. It is, however, appreciated that the rotational transmission described above is more intuitive and has a simpler construction.

According to another embodiment, the cartridge constitute the whole front part of the injection device. Thereby, hygienic advantages are obtained.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An exchangeable cartridge containing a liquid composition, for an injection device for delivering the liquid composition, said cartridge comprising:
   a plunger connectable with a plunger rod of the injection device, wherein the plunger comprises a rod connector connectable with a front end portion of the plunger rod, the rod connector having an entrance opening defined by wall sections of the rod connector, a width of the entrance opening being smaller than a maximum width of the front end portion, and a width of a rod portion adjacent to and rear of the front end portion at most corresponding to the width of the entrance opening, wherein the wall sections are resilient for enabling the front end portion to pass the entrance opening upon exerting an opening force on the wall sections, wherein the rod connector comprises a rod stop portion, wherein a distance between the entrance opening and the rod stop portion exceeds a length of the front end portion, which enables a longitudinal play between the front end portion of the plunger rod and the entrance opening and the rod stop portion, when the rod connector is connected to the front end portion, thereby enabling the front end portion to move back and forth between the entrance opening and the rod stop portion without moving the plunger for allowing a pressure release of the liquid composition within the cartridge without actively moving the plunger rearwards, wherein a proximal portion of the front end portion of the plunger rod defines a diameter larger than the entrance opening, and a distal portion of the front end portion is conical-shaped and defines a diameter smaller than the entrance opening, an entire extent of an automatic rearward movement of the plunger rod being performed without the plunger rod causing the plunger to move rearwards.

2. An injection device for delivering a liquid composition, comprising:
an exchangeable cartridge and a generally elongated housing, said housing comprising a drive device, and a plunger rod connected with the drive device, said exchangeable cartridge containing a liquid composition, a plunger connected with the plunger rod, wherein the plunger comprises a rod connector connectable with a front end portion of the plunger rod, the rod connector having an entrance opening defined by wall sections of the rod connector, a width of the entrance opening being smaller than a maximum width of the front end portion, and a width of a rod portion adjacent to and rear of the front end portion at most corresponding to the width of the entrance opening, wherein the wall sections are resilient for enabling the front end portion to pass the entrance opening upon exerting an opening force on the wall sections, wherein the rod connector comprises a rod stop portion, wherein a distance between the entrance opening and the rod stop portion exceeds a length of the front end portion, which enables a longitudinal play between the front end portion of the plunger rod and the entrance opening and the rod stop portion, thereby enabling the front end portion to move back and forth between the entrance opening and the rod stop portion without moving the plunger, wherein the drive device is configured to automatically move the plunger rod rearwards after being operated for moving the plunger rod forwards, the moving of the plunger rod forwards causing injection of an amount of the liquid composition, wherein a length of a rearward movement of the plunger rod is less than the distance between the entrance opening and the rod stop portion, an entire extent of an automatic rearward movement of the plunger rod being performed without the plunger rod causing the plunger to move rearwards.

3. The injection device according to claim 2, wherein the rod connector comprises a base portion connected with the wall sections at a front end of the wall sections.

4. The injection device according to claim 3, wherein the rod stop portion is connected with the base portion.

5. The injection device according to claim 4, wherein at least one of the wall sections comprises an inner surface, and a heel portion extending radially inwards from the inner surface at a rear end of the wall section, at said entrance opening.

6. The injection device according to claim 5, wherein said at least one of the wall sections comprising a resilient portion protruding from an outer surface of said at least one of the wall sections and being arranged to abut against an inner surface of a liquid container comprised in the cartridge.

7. The injection device according to claim 5, wherein said at least one of the wall sections has a front wall portion, connected with the base portion, and a rear wall portion connected with the front wall portion via a flexible joint.

8. The injection device according to claim 2, wherein the front end portion of the plunger rod comprises a circumferential engagement surface at a rear end of the front end portion, wherein the wall sections comprise at least one complementary engagement surface for engagement with the engagement surface of the plunger rod, at the entrance opening, said at least one complementary engagement surface comprising an inclined surface leaning inwards in a rearward direction.

9. The injection device according to claim 2, wherein the rod stop portion comprises a centre pin protruding rearwards from a front end of the rod connector at a centre thereof.

10. The injection device according to claim 2, wherein the wall sections are arranged such that a spring force of the wall sections is large enough to keep the entrance opening in its idle position during a rearward movement of the plunger, by the plunger rod when the front end portion is connected with the rod connector, from a position between the ends of the cartridge, while being weak enough to enable withdrawal of the front end portion from the rod connector when the plunger reaches its rearmost position.

11. An injection device for delivering a liquid composition, comprising:
a generally elongated housing, arranged to hold an exchangeable cartridge, containing a liquid composition for delivering the liquid composition, said housing comprising a drive device, and a plunger rod connected with the drive device, said cartridge comprising a plunger connectable with the plunger rod, wherein the plunger comprises a rod connector connectable with a front end portion of the plunger rod, the rod connector having an entrance opening defined by wall sections of the rod connector, a width of the entrance opening being smaller than a maximum width of the front end portion, and a width of a rod portion adjacent to and rear of the front end portion at most corresponding to the width of the entrance opening, wherein the wall sections are resilient for enabling the front end portion to pass the entrance opening upon exerting an opening force on the wall sections, wherein the rod connector comprises a rod stop portion, wherein a distance between the entrance opening and the rod stop portion exceeds a length of the front end portion, which enables a longitudinal play between the front end portion of the plunger rod and the entrance opening and the rod stop portion, when the rod connector is connected to the front end portion, thereby enabling the front end portion to move back and forth between the entrance opening and the rod stop portion without moving the plunger, wherein the drive device is configured to automatically move the plunger rod rearwards after being operated for moving the plunger rod forwards, the moving of the plunger rod forwards causing injection of liquid, wherein a length of a rearward movement of the plunger rod is less than the distance between the entrance opening and the rod stop portion, an entire extent of an automatic rearward movement of the plunger rod being performed without the plunger rod causing the plunger to move rearwards.

12. The injection device according to claim 11, wherein the front end portion of the plunger rod comprises a frustoconical portion having its top at the front end of the plunger rod.

13. The injection device according to claim 11, wherein the front end portion of the plunger rod comprises a circumferential engagement surface at a rear end of the front end portion, the engagement surface being arranged to engage with the plunger, at the entrance opening, for moving the plunger rearwards when the plunger rod is moved rearwards.

14. The injection device according to claim 11, wherein the plunger rod is rotatably attached for rotation about a longitudinal axis thereof, and is arranged to be rotated in order to be longitudinally moved.

* * * * *